(12) United States Patent
Jelinek

(10) Patent No.: US 7,855,073 B2
(45) Date of Patent: Dec. 21, 2010

(54) CELLS CONTAINING A NANOPATCH SENSOR IN THEIR MEMBRANE

(75) Inventor: Raz Jelinek, Reut (IL)

(73) Assignee: Ben-Gurion University of the Negev Research and Development Authority, Beer-Sheva (IL)

(*) Notice: Subject to any disclaimer, the term of this patent is extended or adjusted under 35 U.S.C. 154(b) by 908 days.

(21) Appl. No.: 10/573,814

(22) PCT Filed: Sep. 28, 2004

(86) PCT No.: PCT/IL2004/000899

§ 371 (c)(1),
(2), (4) Date: Mar. 28, 2007

(87) PCT Pub. No.: WO2005/031348

PCT Pub. Date: Apr. 7, 2005

(65) Prior Publication Data

US 2007/0275433 A1    Nov. 29, 2007

(30) Foreign Application Priority Data

Sep. 30, 2003    (IL) ..................................... 158173

(51) Int. Cl.
*C12N 5/00*    (2006.01)
(52) U.S. Cl. ................. 435/325; 435/243; 435/440
(58) Field of Classification Search ............... None
See application file for complete search history.

(56) References Cited

U.S. PATENT DOCUMENTS 5,156,810 A * 10/1992 Ribi .................. 422/82.01

OTHER PUBLICATIONS

Johnston D.S. et al. Phospholipid polymers-synthesis and spectral characteristics, Biochimica et Biophysica Acta, 1980, vol. 602, pp. 57-69.*

Alonso A. et al. Polymerisation of diacetylene fatty acid in cultures of Bacillus cereus, Biochimica et Biophysica Acta, 1982, vol. 712, pp. 292-298.*

Leaver J. et al. The biosynthetic incorporation of diacetylene fatty acids into the biomembrane of *Acholeplasma laidlawii* A cells and polymerisation of the biomembranes by irradiation with ultraviolet light, Biochimica et Biophysica Acta, 1983, vol. 727, pp. 327-335.*

Jelinek R. et al. Interfacial catalysis by phospholipases at conjugated lipid vesicles: colorimetric detection and NMR spectroscopy, Chemistry & Biology, Nov. 1998, vol. 5, No. 11, pp. 619-629.*

International Search Report for PCT/IL2004/000899 dated Feb. 14, 2005.

Rozner et al., *Detection and analysis of membrane interactions by a biomimetic colorimetric lipid/polydiacetylene assay*, Analytical Biochemistry, vol. 319, No. 1, Aug. 1, 2003, pp. 96-104, XP004434052.

Kolusheva et al., *Rapid Colorimetric Detection of Antibody-Epitope Recognition at a Biomimetic Membrane Interface*, Journal of the American Chemical Society, vol. 123, 2001, pp. 417-422, XP002280715.

Evrard Damien et al., *A new colorimetric assay for studying and rapid screening of membrane penetration enhancers*, Pharmaceutical Research, vol. 18, No. 7, Jul. 2001, pp. 943-949, XP002313898.

Kolusheva et al., *Biomimetric lipid/polymer colorimetric membranes: Molecular and cooperative properties*, Journal of Lipid Research, vol. 44, No. 1, Jan. 2003, pp. 65-71, XP002313899.

Song et al., *Smart Materials for Biosensing Devices: Cell-mimicking Supramolecular Assemblies and Colorimetric Detection of Pathogenic Agents*, Biomedical Microdevices, vol. 4, No. 3, 2002, pp. 213-221, XP008030659.

Jelinek et al., *Polymerized lipid vesicles as colorimetric biosensors for biotechnological applications*, Biotechnology Advances, vol. 19, No. 2, Apr. 1, 2001, pp. 109-118, XP004240663.

Halevy Revital et al., *Membrane binding and permeation by indolicidin analogs studied by a biomimetic lipid/polydiacetylene vesicle assay*, Peptides, vol. 24, No. 11, Dec. 2003, pp. 1753-1761, XP002313900.

Jianrong et al., *Nanotechnology and biosensors*, Biotechnology Advances, vol. 22, No. 7, Sep. 2004, pp. 505-518, XP004522070.

* cited by examiner

*Primary Examiner*—Jon P Weber
*Assistant Examiner*—Satyendra K Singh
(74) *Attorney, Agent, or Firm*—Nixon & Vanderhye P.C.

(57) ABSTRACT

The present invention provides isolated cells comprising nanopatch sensors integrated into the cell membrane thereof, wherein said sensors are provided in the form of perturbation-sensitive constructs, and wherein said perturbation-sensitive constructs respond to perturbations of the cell membrane by means of a detectable change in one or more physical or chemical properties associated with said construct.

30 Claims, 15 Drawing Sheets

CELLS CONTAINING A NANOPATCH SENSOR IN THEIR MEMBRANE

This application is the U.S. national phase of international application PCT/IL2004/000899 filed 28 Sep. 2004, which designated the U.S. and claims benefit of IL 158173, filed 30 Sep. 2003, the entire contents of each of which are hereby incorporated by reference.

FIELD OF THE INVENTION

The present invention relates to a novel cellular platform for detecting the presence of agents and conditions that cause changes in the conformation and/or function of the cell membrane, and/or are involved with biochemical processes occurring at the cell-membrane surface. More specifically, the present invention provides a colorimetric/fluorescent sensor of membrane perturbations that may be incorporated into the cell membrane of living cells.

BACKGROUND OF THE INVENTION

There currently exist a number of different probes that may be used for investigating cellular processes in vivo and in vitro. Most of these probes, and the techniques associated therewith fall into one of the following two categories:

a) radioactive, fluorescent or other readily-detectable labels that may be inserted or embedded into the cellular framework, such that specific chemical pathways and/or individual molecular entities may be studied;

b) simple visualization tools for investigating activity, either within cellular compartments or at the level of the whole cell.

There is, however, a need for techniques that can enable real-time reporting of biological or chemical events that may affect the function and/or morphology and/or structural properties of either the cell membrane, or alternatively, the function, morphology and viability of the whole cell. A key feature of these desired techniques is that they will not be limited to any specific molecule, molecular pathway or specific cell type or cell line.

A number of prior art publications disclose the use of polydiacetylene-based means for detecting membrane-perturbing events and/or agents:

WO 98/39632 suggests the use of polydiacetylenes for detecting reactions, by means of exposing the reaction means to a biopolymeric material comprising said polydiacetylenes. Preferably, the biopolymeric material is provided in the form of liposomes, films, tubules and other membrane-simulating forms.

WO 99/10743 describes the encapsulation of polydiacetylenes into metal oxide glass, and the use of the transparent composite obtained for the detection of various analytes.

WO 00/55623 discloses a beneficial combination of polydiacetylenes, lipids and suitable means linked thereto for detecting the presence of analytes in a liquid sample, wherein said analytes cannot react chemically with said polydiacetylenes and lipids. Specifically mentioned analytes include metal ions, biological ligands and peptides.

It is to be noted, however, that none of the foregoing publications disclose the use of the polydiacetylene construct in living cells.

Other publications have disclosed detection systems for use inside the outer membranes of living cells. WO 95/27204, for example, discloses a method for detecting and measuring molecules located at the cell surface (e.g. receptors), wherein said method involves labeling the cells with a molecular probe comprising a lipophilic moiety and a reporter moiety, preferably a fluorescence-emitting reporter moiety.

It is a purpose of the present invention to provide a method for "engineering" cells such that they contain within their outer membrane a membrane perturbation-detecting construct.

It is another purpose of the invention to provide the aforementioned engineered cells in a viable form such that they may be used as an assay system for detecting and/or measuring changes in the conformation and/or function of their cell membrane and processes occurring at the membrane surface.

It is a further purpose of the invention to provide a method for detecting and/or measuring the presence of agents and conditions that cause changes in cell membrane function and/or structure and processes occurring at the membrane surface, said method involving the use of the aforementioned engineered cells.

Further objects and advantages of the present invention will become apparent as the description proceeds.

SUMMARY OF THE INVENTION

It has now been surprisingly found that a chemical construct comprising polydiacetylenes and lipids may be assembled within the cell membrane of living cells, and that said construct retains its ability to undergo its characteristic chromatic (red to blue) transition and associated fluorescent emission in live cells in response to various perturbing agents and conditions. It has further been unexpectedly found that following insertion of said construct into the cell membrane of living cells, the viability of said cells is retained for a period of time that is sufficient to permit the use of said cells as a system for detecting and/or quantifying biochemical events that lead to structural and morphological changes in the cell membrane and/or other processes occurring at the surface of the cell membrane.

The present invention is primarily directed to isolated cells comprising nanopatch sensors which are integrated into the cell membrane thereof, wherein said sensors are provided in the form of perturbation-sensitive constructs, wherein said perturbation-sensitive constructs respond to perturbations of the cell membrane by means of a detectable change in one or more physical or chemical properties associated with said construct.

The term "nanopatch sensors" is used to indicate that the perturbation-sensitive constructs are present within the cell membrane as discrete patches having dimensions in the range of 10 nanometers to several hundreds of nanometers.

The term "perturbations of the cell membrane" is used herein to indicate any changes in the three-dimensional conformation and/or function of said cell membrane. Included within this definition are perturbations of the cell membrane that may lead to the aforementioned changes in function thereof, even when unaccompanied by any detectable or measurable conformational changes. In addition, the term includes within its scope biochemical processes that occur at the cell membrane surface which, while they do not cause significant structural or functional changes within the membrane itself, may result in the generation of signals that may be detected by the nanopatch sensors of the present invention. Examples of such biochemical processes include the interaction of ligands with their specific receptors, the outward passage of compounds from the cell (e.g. secretory processes) and induction of signaling processes (including such processes having their origin within the cytoplasm).

The aforementioned physical or chemical property associated with the construct may be any property or function that may be readily detected and/or measured. Preferably, such a property will be a form of electromagnetic radiation, such as visible light or ultraviolet or infrared radiation. Most preferably, the detected property will be a chromatic transition (e.g. a change in visible color of the cells or portions thereof) or a fluorescence emission. Consequently, in one preferred embodiment of the isolated cells of the present invention, the detectable change in the physical or chemical properties associated with the perturbation-sensitive constructs is a change in the visible range absorption spectrum of said cells. In another such preferred embodiment, the detectable change in the physical or chemical properties is a change in the fluorescent emission spectrum of the cells.

In one preferred embodiment of the present invention, the aforementioned construct comprises a polymer associated with one or more lipid components. In a particularly preferred embodiment of the invention, the polymer is polydiacetylene (PDA). In an even more particularly preferred embodiment, the PDA is a polymer of 10,12-tricosadionic acid, and the lipid components are selected from the group consisting of dimyristoylphosphatidyl-glycerol, dimyristoylphosphatidylcholine and dimyristoylphosphatidylethanolamine.

When the polymer incorporated into the aforementioned construct is PDA, the detectable properties associated therewith are a blue-to-red color transition, and a fluorescent emission at 560 nm emitted from the red phase of the polymer.

In another aspect, the present invention is also directed to a process for producing living cells comprising the aforementioned nanopatch sensors, said process comprising the steps of preparing an aqueous solution comprising the perturbation-sensitive construct, or precursors thereof, and co-incubating a suspension of said living cells with said construct or with said precursors, such that said construct becomes integrated into the cell membrane of said living cells. The abovementioned aqueous solution may comprise any water-based medium that is suitable for use together with living cells, and is preferably a buffered solution.

In one preferred embodiment of the process of the invention, the perturbation-sensitive construct comprises a polymerizable material associated with one or more lipid components, and said process further comprises polymerization-inducing short ultraviolet irradiation of said construct following co-incubation with the living cells.

In a particularly preferred embodiment of the process of the invention, the aforementioned polymerizable material is a monomer that may be polymerized to form PDA. In an even more particularly preferred embodiment, the monomer is 10,12-tricosadionic acid, and the lipid components are selected from the group consisting of dimyristoylphosphatidyl-glycerol, dimyristoylphosphatidylcholine and dimyristoylphosphatidylethanolamine.

In a further aspect, the present invention also provides a method for detecting and/or measuring agents and conditions that cause perturbations in the cell membranes of living cells, wherein said method comprises the steps of introducing nanopatch sensors into said living cells in accordance with the process disclosed hereinabove, exposing said nanopatch sensor-containing cells to a known or putative perturbation-inducing agent or condition, and detecting and/or measuring one or more changes in the physical or chemical properties associated with said nanopatch sensors.

In one preferred embodiment of the method of the invention, the perturbation-sensitive construct contained within the nanopatch sensors comprises a polymer associated with one or more lipid components. In a particularly preferred embodiment of this aspect of the invention, the polymer is PDA. In an even more particularly preferred embodiment, the diacetylene polymer is a polymer of 10,12-tricosadionic acid, and the lipid components are selected from the group consisting of dimyristoylphosphatidyl-glycerol, dimyristoylphosphatidylcholine and dimyristoylphosphatidylethanolamine.

In one particularly preferred embodiment of this aspect of the invention, the change in the physical or chemical properties associated with said nanopatch sensors to be detected and/or measured is a change in the visible range absorption spectrum of said sensors.

In another particularly preferred embodiment of this aspect of the invention, the change in the physical or chemical properties associated with said nanopatch sensors to be detected and/or measured is a change in the fluorescent emission spectrum of said sensors.

In a further aspect, the isolated cells comprising nanopatch sensors are prokaryotic cells, wherein said sensors are integrated into the cell wall and/or cell membrane thereof, and wherein said sensors are provided in the form of perturbation-sensitive constructs, and wherein said perturbation-sensitive constructs respond to perturbations of the cell wall and/or of the underlying cell membrane by means of a detectable change in one or more physical or chemical properties associated with said construct.

In one preferred embodiment, the perturbation-sensitive constructs of the aforementioned isolated prokaryotic cells comprise a PDA polymer associated with one or more lipid components selected from the group consisting of dimyristoylphosphatidylglycerol, dimyristoylphosphatidylcholine and dimyristoylphosphatidylethanolamine.

In one preferred embodiment of the aforementioned isolated prokaryotic cells, the detectable change in the physical or chemical properties associated with the perturbation-sensitive constructs is a change in the visible range absorption spectrum of said cells.

In another preferred embodiment, the detectable change in the physical or chemical properties associated with the perturbation-sensitive constructs is a change in the fluorescent emission spectrum of said cells.

In another aspect, the present invention is directed to a process for producing living prokaryotic cells comprising the aforementioned nanopatch sensors, wherein said prokaryotic cells have a cell wall as their outer layer, and wherein said process comprises the steps of preparing an aqueous solution comprising the perturbation-sensitive construct, or precursors thereof, and co-incubating a suspension of said living cells with said construct or construct precursors, such that said construct becomes integrated into the cell wall and/or cell membrane of said cells.

In a preferred embodiment, the perturbation-sensitive construct used in the aforementioned process comprises a polymerizable material associated with one or more lipid components, and said process further comprises polymerization-inducing short ultraviolet irradiation of the said construct following co-incubation with the living cells.

In a particularly preferred embodiment, the polymerizable material is 10,12-tricosadionic acid, and the lipid components are selected from the group consisting of dimyristoylphosphatidylglycerol, dimyristoylphosphatidylcholine and dimyristoylphosphatidylethanolamine.

The present invention also provides a method for detecting and/or measuring agents and conditions that cause perturbations in the cell walls and cell membranes of living cell-wall containing prokaryotic cells, wherein said method comprises the steps of providing isolated nanopatch sensor-containing cells as described hereinabove, exposing said nanopatch sensor-containing cells to a known or putative perturbation-inducing agent or condition, and detecting and/or measuring one or more changes in the physical or chemical properties associated with said nanopatch sensors.

In one preferred embodiment of the aforementioned method, the perturbations comprise changes in the three-dimensional conformation of the cell wall and/or cell membrane.

In another preferred embodiment, the perturbations comprise changes in the function of the cell wall and/or cell membrane.

In another preferred embodiment of the aforementioned method, the perturbations are caused by biochemical processes occurring at the cell wall surface and/or cell membrane surface, wherein said processes do not cause any significant structural or functional changes within said cell wall and/or cell membrane.

All the above and other characteristics and advantages of the present invention will be further understood from the following illustrative and non-limitative examples of preferred embodiments thereof.

DETAILED DESCRIPTION OF PREFERRED EMBODIMENTS

Figure 1:
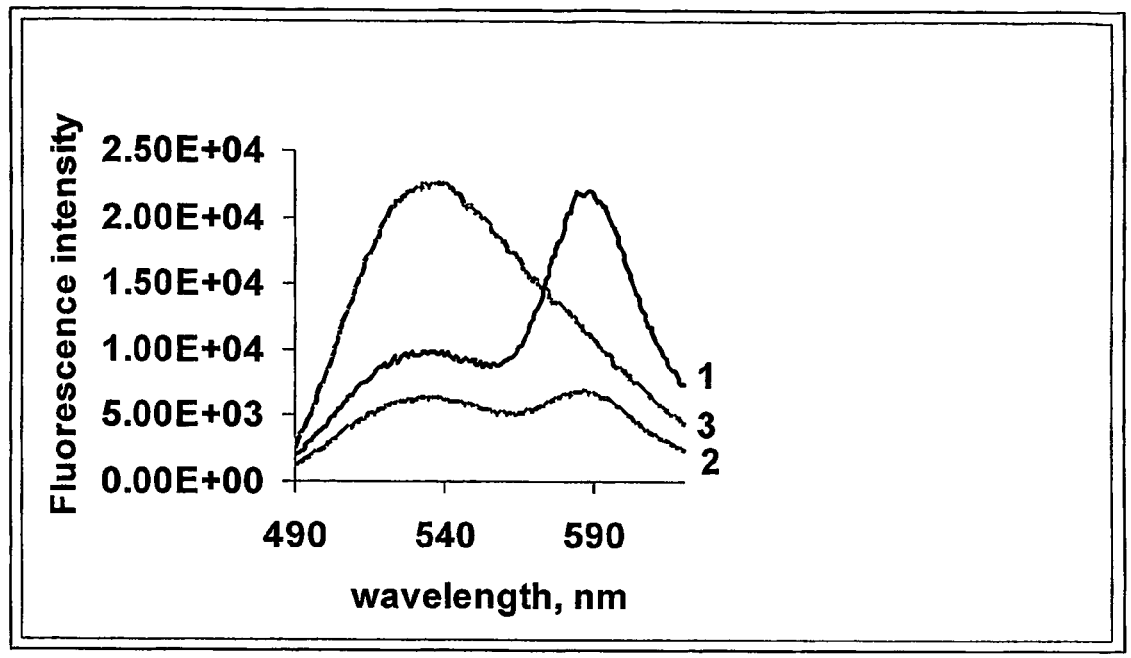
FIG. 1 graphically depicts the changes in the fluorescent spectra of NBD-PE and rhodamine incorporated within the lipid/PDA constructs upon association with U937 cells. The spectra indicate that significant integration of lipid/PDA construct within the cell membrane occurs.
Figure 2A:
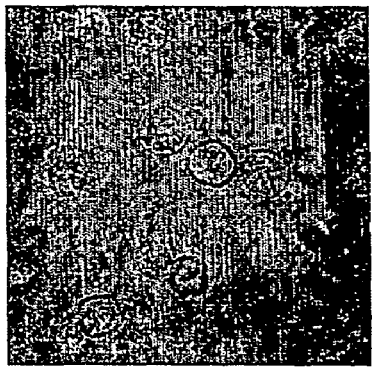
FIG. 2 presents a set of visible microscopy images [top] and fluorescence microscopy images [bottom] showing lipid/PDA/U937 cell constructs in the initial blue phase [left] and red phase (induced by rapid heating) [right].
Figure 2B:
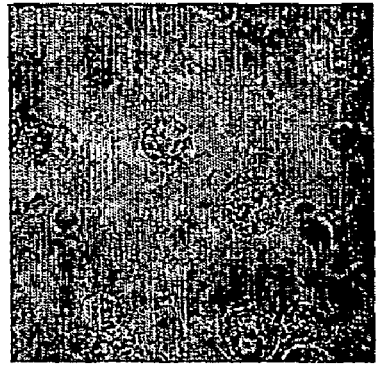
Figure 2C:
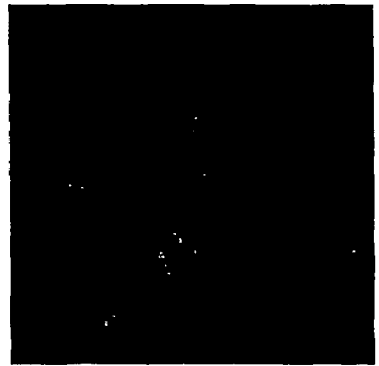
Figure 2D:
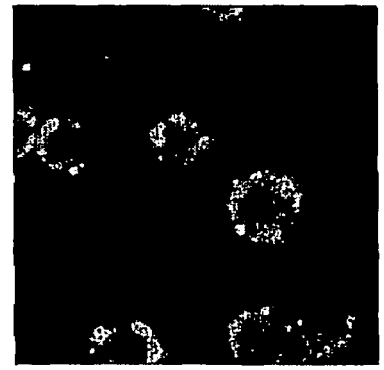

The present invention relates to a real-time novel cellular platform which may be used for detecting occurrence of cellular biochemical processes that involve membrane perturbation or take place at membrane surfaces. In contrast to the prior art cellular assays which, in general, detect specific chemical species or pathways with in the cell, the cells and methods of the present invention are sensitive to any stimuli that induce functional and morphological modification of the cell membrane. A key feature of the claimed invention is the fact that following introduction of the nanopatches into the cell membrane, the target cells remain alive (and therefore useful for real-time investigations of processes in viable cells) for periods of at least four hours.

The above-disclosed nanopatches may be incorporated into the cell membranes and/or cell walls of live prokaryotic cells (e.g. bacterial species) as well as the cell membranes of live eukaryotic cells, including mammalian cell types such as epithelial cells, erythrocytes, monocytes, red blood cells, platelets and neurons. It is to be emphasized that the immediately preceding list of cell types is given for illustrative purposes only, and is not to be construed as limiting the scope of the invention in any way. Rather, the invention presently disclosed and claimed may be used in conjunction with many other cell types, originating from a variety of species. Both cultured cells (primary cultures and established cell lines) and freshly-isolated cells (e.g. from blood separations) may be used according to the method and preparative process of the present invention. In the case of prokaryotic cells, it should be noted that in certain bacterial species, the nanopatches of the present invention may actually be integrated into the outer cell wall of the organism (as well into the cell membrane), and in those circumstances, used to detect changes that occur in, and in close proximity to, said cell wall as well as changes involving the underlying cell membrane. Consequently, the isolated cells, preparative process and method of the present invention may also be applied to the situation wherein the cells are prokaryotic cells having a cell wall as their outermost layer, and wherein the nanopatches are incorporated into said cell wall rather than into the cell membrane.

The most preferred polymer for use in preparing the perturbation-sensitive construct of the present invention is polydiacetylene, obtained by the polymerization of monomers selected from the group of diacetylene lipid acids and diacetylene derivatives, such as, for example, tricosadiynoic acid, tricosadiynoic methyl esters, pentacosadiynoic acid and pentacosadiynoic methyl esters. In the absence of membrane perturbation, polydiacetylene absorbs light at a first wavelength which is approximately 640 nm. In the presence of an agent, state or condition that causes a structural and/or functional change in the cell membranes of the cells being studied, or biochemical processes occurring at the cell membrane that perturb the lipid/PDA construct, the absorption is shifted to a second wavelength, which is approximately 520 nm. Thus, a color transition from blue to red indicates that the aforementioned structural and/or functional changes in the membranes or biochemical processes associated with membranes have taken place.

Preferred diacetylene monomers that may be used according to the present invention for preparing the chromatic polydiacetylenes are well known in the art and are described, inter alia, in WO 99/10743 and US 2002/0034475, which are incorporated herein by reference.

Most preferably, the monomers are selected from the group consisting of 10,12-tricosadiynoic acid, 10,12-pentacosadiynoic acid, 10,12-octadecadiynoic acid, 5,7-docosadiynoic acid, 5,7-pentacosadiynoic acid and 5,7-tetracosadiynoic acid. These monomers are all commercially available.

Preferred lipids that may be used according to the present invention include, but are not limited to, glycolipids, phospholipids, lipopolysaccharides, steroids and alcohol derivatives thereof, extracts of lipids of the cell membrane obtained from various microorganisms as well as other components of the cell membrane. Particularly preferred lipids are selected from the group consisting of dimirystoylphosphatydilcholine (DMPC), phophatyldilglycerole (PG) dipalmitoylphosphatidylcholine (DPPE), natural phosphatydilcholine (PC), dimirystoylphosphatidylcholine (DMPG), cardiolipin, dimyristoylphosphatyldiserine (DMPS), sphingomyelin, ceramide, galactosylderamide, and cholesterol, or mixtures thereof.

The above-disclosed nanopatch sensors comprising polydiacetylene and lipids exhibit visible blue to red transitions, when subjected to membrane-perturbing agents and conditions. This chromatic transition can be observed by the naked eye. Alternatively, the color changes may be recorded and/or quantified by means of UV/visible spectrophotometry using a standard spectrophotometer or an ELISA plate reader. Typically, the spectrophotometric reading is made at 27° C. using a 1 cm optical path cell with a standard laboratory spectrophotometric device such as the Hewlett-Packard 8452A diode array spectrophotometer.

The quantitative measurement of the color transition exhibited by the perturbation-sensitive constructs following disturbance to the cell membrane conformation and/or function may be carried out similarly to the description given in WO 00/55623, which is incorporated herein by reference.

The fluorescent emission associated with the chromatic transition may be detected by any suitable technique, for example, by the use of an inverted microscope fitted with fluorescent excitation and detection means, or by the use of a laser scanning confocal microscope. Quantitative measurements of both the fluorescent emission and the chromatic transition may be made using the abovementioned microscopic techniques coupled with suitable image analysis apparatus and algorithms.

The aforementioned fluorescent emission may also be detected and/or measured by means of fluorescence spectroscopy, using a conventional spectrofluorimeter as is well known in the art.

The method for detecting and/or measuring agents and conditions that cause perturbations in the cell membranes of living cells that was disclosed hereinabove may be employed to detect and/or measure changes in membrane conformation and/or function that result from the chemical and physical modifications caused by many different agents and conditions. The following short list of possible applications of the claimed method is by no means exhaustive and is intended to be illustrative rather than limiting:

1. Detection of changes in osmotic pressure of the extracellular environment.

Colorimetric/fluorescence transitions occur when cells are placed in a solution having a high osmotic pressure (e.g. a concentrated sucrose solution). Thus, the osmotic gradient created by increasing the osmotic pressure of the medium in which the cells are contained causes distortion of the cell morphology and membrane disruption, giving rise to the observed changes in the nanopatch sensor color and fluorescence.

2. Detection or measurement of changes of membrane effects following the action of membrane-active peptides.

Membrane-active peptides, such as cytolytic and hemolytic peptides, generally penetrate and disrupt the cellular membrane by means of pore formation and/or membrane micellization and/or other membrane perturbation processes. Following such disruption, the characteristic chromatic transition and fluorescent emission of the nanopatch sensor may be detected and measured.

3. Detection and Measurement of Apoptosis-Inducing Substances

The chromatic cellular assembly can detect morphological changes in the cells which occur following induction of apoptotic or necrotic processes induced by various substances interacting with the cell.

4. Lipid Fusion Processes

The engineered cells of the present invention can be used to report the occurrence of fusion events such as the fusion of vesicles and lipoplexes with the cellular membrane, as well cell-cell fusion processes.

5. Drug Action and Other Receptor-Mediated Processes

The presently-claimed nanopatch-containing cells may also be used to detect the penetration of drugs and other ligands into said cells and the subsequent binding of these ligands to their specific receptors. Such ligands can include naturally-occurring messengers, chemical mediators and modulators, as well as pharmacological agents.

In addition to the applications given in the foregoing list, the nanopatch-containing cells of the present invention may be used to detect the presence of various analytes that are capable of interacting with cellular membranes, including microorganisms and toxins produced thereby, metal cations, peptides, proteins, biological ligands and pharmaceutically active compounds.

Metal cations that may be detected according to the present invention include alkali or alkaline-earth metals, as well as transition metals.

Peptides that may be detected by the method of the present invention include antimicrobial peptides, membrane-active peptides and cytolytic peptides. The peptides may contain between 5 to 100 amino acids, and may have hydrophobic and amphipathic domains.

Pharmaceutically active compounds that may be detected by the method of the present invention include, but are not limited to, hydrophobic compounds having molecular weight of below 1000 g/mol, that are capable of binding and permeating cellular membrane or physiological lipid barriers, such as drugs, metabolites and penetration enhancers.

Proteins that may be detected by the method of the present invention include, but are not limited to, membrane proteins, lipophilic enzymes and signaling proteins. Other biological ligands that may be detected by the method of the present invention include hormones and biological compounds that specifically bind or permeate cellular membranes or have specific affinities to membrane receptors.

The above-described potential uses of the isolated cells and methods of the present invention are provided for the sake of illustration only, and are not intended to be limiting in any way. Thus, the claimed isolated cells and associated method could be used for the detection of diverse biological and pharmacological processes (in addition to those described hereinbefore) including viral fusion, cell-cell communication and gene therapy, as well as all other processes, agent-mediated actions and states that require the involvement of the cell membrane.

The following examples are provided for illustrative purposes and in order to more particularly explain and describe the present invention. The present invention, however, is not limited to the particular embodiments disclosed in the examples.

EXAMPLE 1

Preparation of Bio-Engineered Cells 1.1 Cell Cultures 1.1.1 Suspension Culture Cells Cells of the U937 human promonocytic leukemia cell line were cultured in RPMI 1640 culture medium supplemented with 10% fetal calf serum (FCS) and 1% penicillin/streptomycin, using a standard cell culture incubator at 37° C. under a 5% $CO_2$ atmosphere. The cells were maintained at a density of $5 \times 10^5$ cells/ml.

1.1.2 Adenocarcinoma Cells

MCF-7 human breast adenocarcinoma cells were grown as a monolayer culture in DMEM medium supplemented with 10% FCS, 2 mM L-glutamine and 1% penicillin/streptomycin in 60 mm culture dishes. The cells were incubated at 37° C. in a humidified incubator in a 5% $CO_2$ environment. The cultured cells were regularly examined using an inverted microscope.

1.1.3 CHO Cells

CHO cells were cultured in F-12 medium supplemented with 5% FCS, 1% L-glutamine, 1% Penicillin/Streptomycin and HEPES 1 mM.

1.2 Preparation of the Lipid/Polymer Nanopatch Sensor

The PDA monomeric unit 10,12-tricosadiynoic acid (TRCDA) and lipid components such as dimyristoylphosphatidylglycerol, dimyristoylphosphatidylcholine and dimyristoylphosphatidylethanolamine were mixed together in different ratios and diluted in a solvent system comprising chloroform:methanol (1:1), and dried under vacuum. The preparation was then sonicated in deionized water at approximately 70° C., cooled at room temperature and kept at 4° C. overnight. The final total lipid concentration was approximately 3 mg/ml.

1.3 Fusion of the Nanopatch Sensor Within the Cell Membrane of the Cultured Cells Cells from suspensions were harvested from the growth medium and washed in buffer (HEPES 20 mM, NaCl 137 mM, KCl 2.7 mM, $KH_2PO_4$ 1 mM, Glucose 25 mM, pH 7.6) using centrifugation at 250 g for 7 minutes.

Approximately two million cells were re-suspended in 2 ml of base buffer to which the lipid/monomer aqueous solution was added to a final lipid concentration of 0.3 mg/ml, and incubated for 30 minutes under slow shaking (65 rpm) at 25° C. Fusion was stopped by washing the cells three times with the base buffer.

The lipid/monomer/cell composites were then irradiated at 254 nm for 20-30 sec in order to induce polymerization of the PDA, yielding polymerized blue cell suspensions. Prior to experiments with external stimuli the "blue" cell pellets ($5 \times 10^6$ cell/ml) were re-suspended in base buffer.

EXAMPLE 2

Determination of Extent of Lipid/PDA Fusion in Bio-Engineered Cells

The extent of fusion between the lipid/PDA nanopatch sensors and the cell membranes of the cells into which said sensors were inserted (performed as described in Example 1), was determined using a resonance energy transfer technique, as described in Struck, D. K. et al., Biochemistry 20: 4093-4099 (1981). Briefly, 125 μl of lipid/PDA monomer suspension containing the fluorescent compounds N-(7-nitro-2,1,3-benzoaxaiazol-4-yl)phosphatidylethanolamine (N—NBD-PE) and N-(lissamine Rhodamine B sulfonyl) dioleoylphosphatidylethanolamine (N—Rh-PE) were added to 1 ml of buffer containing approximately two million monocytic cells. Fusion of the lipid/PDA monomers with the cell membranes was allowed to proceed for 0.5 hour at 25° C. under shaking. Following washing and centrifugation, the cell pellets were resuspended in the same buffer. Emission spectra of the cell suspensions at 536 nm (for N—NBD-PE) and 585 nm (for N—Rh-PE) were then obtained at 25° C., using an Edinburgh FL920 spectrofluorimeter (Edinburgh, UK) at an excitation wavelength of 469 nm.

The results obtained in these spectrofluorimetric investigations are shown graphically in FIG. 1. Line 1 of the figure shows the fluorescence emission spectrum of the aforementioned mixture of lipid/PDA construct precursors containing N—NBD-PE and N—Rh-PE. The 536 nm peak due to NBD emission is small, as a result of energy transfer from NBD to rhodamine.

Line 2 of the figure represents the corresponding spectrum for cells containing the lipid/PDA/rhodamine/NBD construct following fusion of said construct within the cell membrane. Comparison of lines 1 and 2 indicate that following fusion (line 2), the ratio between the 536 nm and 585 nm peaks increases, as a consequence of increased separation distance, thereby reducing the amount of energy transfer from NBD to rhodamine. These spectrofluorimetric results thus indicate that the above-described method leads to significant integration of the lipid/PDA construct within the cell membrane.

As a control experiment, the construct-containing cells were then treated with 1% Triton X-100 for a minimum of ten seconds at 25° C. The fluorescence spectrum of these treated cells (line 3) indicates that the disruption of the cell membrane following surfactant treatment results in loss of the spatial relationships between the various molecules in the membrane (including rhodamine and NBD). Consequently, there is less energy transfer from NBD to rhodamine, and the 536 nm peak is correspondingly larger.

Quantitative results of the resonance energy transfer investigations are summarized in the following table:

| Lipid/PDA monomer composition (mole:mole) | % Fusion with monocytic cells |
|---|---|
| TRCDA/PE/PG (4:1:1) | 58 |
| TRCDA/PE/PG (8:1:1) | 33 |
| TRCDA/PC/PG (8:1:1) | 9 |

EXAMPLE 3

Viability of Bio-engineered Cells

Cell Viability Assays

Viability was estimated by two techniques: trypan blue dye exclusion and acridine orange/ethidium bromide double staining methods.

Trypan Blue Exclusion Method

A small volume of the examined cell suspension was mixed with 0.5% trypan blue in 1:1 (v/v) ratio and incubated for one minute. Following this, approximately 10 µL of the mixture was placed under the microscope and stained cells were counted using a hemocytometer. Non-viable cells absorb the dye and appear blue, while viable cells remain opaque.

Acridine Orange/Ethidium Bromide Staining

Apoptosis was determined morphologically after staining with acridine orange and ethidium bromide and counting viable cells by fluorescence microscopy. Cell density was adjusted to 1×10$^6$ cells/ml in buffer. Acridine orange and ethidium bromide (1:1) (v/v) mixed in PBS (phosphate buffer solution) to a final concentration of 100 µg/ml. 2 µl dye was mixed with 25 µl of cell suspension and cells were immediately checked.

The cellular morphology was evaluated by fluorescence microscopy (Olympus IX70, Japan) using a 20×0.5 objective and an LP520 nm filter. Apoptotic cells were essentially characterized by nuclear condensation of chromatin and/or nuclear fragmentation. Necrotic cells were identified by uniform labeling of the cells with ethidium bromide. About 300 cells were evaluated for apoptosis and/or necrosis for each sample.

The results of the viability study are shown in the following table:

| Time after sensor incorporation | Acridine Orange/Ethidium Bromide | | | | Trypan Blue Live Cells |
|---|---|---|---|---|---|
| | Live | Necrotic | Early Apoptotic | Late Apoptotic | |
| 1.5 hours | 90% | 7% | 3% | 3% | 90% |
| 2 hours | 89% | 2% | 4% | 4% | 89% |
| 3 hours | 66% | 6% | 23% | 4% | 78% |

EXAMPLE 4

Detection of Membrane Perturbations Using Nanopatch-containing U937 Cells

U937 cells were grown and prepared as described in section 1.1 of Example 1, hereinabove. The precursors of the Lipid/PDA constructs (i.e. a mixture of 10,12-tricosadiynoic acid, PE and PG at a molar ratio of 8:1:1) were prepared and introduced into the cells in accordance with the methods described in sections 1.2 and 1.3 of Example 1.

Separate aliquots of cells containing the lipid/PDA constructs were then subjected to the membrane-perturbing treatments described below.

Transmission differential interference contrast (DIC) and fluorescence images of the cells were acquired on a laser scanning confocal microscope (Olympus IX70) with an PlApo 60× objective using oil (NA 1.4). Excitation was at 488 nm using argon laser source. Emitted light was collected through a LP 560 nm filter.

A. Heat Treatment

FIG. 2 demonstrates the chromatic transition (upper photographs) and fluorescent emission (lower photographs) that occur following the application of thermal stress to lipid/PDA nanopatch-containing U937 cells, by means of rapid heating. The upper right photograph shows the appearance of the cells under regular illumination following the thermal stress. (The cells appear red in color photomicrographs.) The lower right photograph shows the fluorescent emission that accompanies the chromatic transition following the thermal stress.

B. Elevation of Osmotic Pressure

Figure 3:
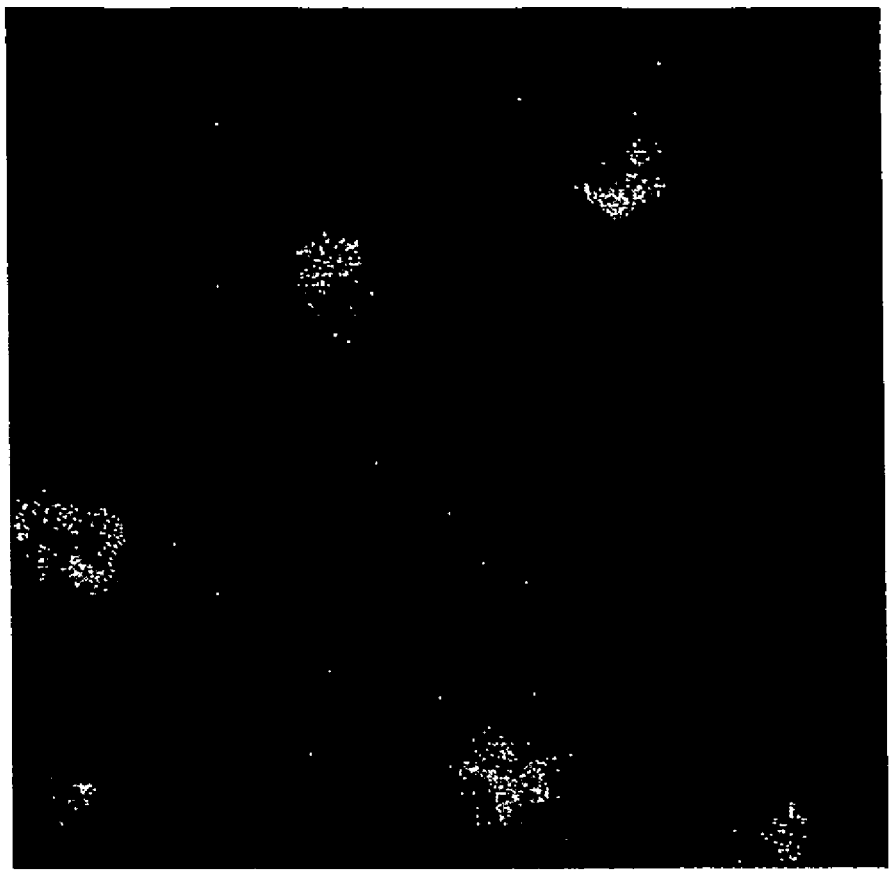
FIG. 3 is a fluorescent photomicrograph depicting the characteristic fluorescence seen after placing U937 cells containing lipid/PDA constructs of the present invention in a high osmotic pressure solution (1 M sucrose).

The photomicrograph shown in FIG. 3 shows the fluorescent emission of the lipid/PDA constructs contained within cells following their exposure to a high osmotic pressure environment (1 M sucrose) at 25° C. for periods of 5 to 15 minutes.

C. Incubation With a Membrane-Active Peptide

Figure 4:
FIG. 4 is a fluorescent photomicrograph depicting fluorescence in U937 cells containing lipid/PDA constructs of the present invention after placing said cells in a solution containing 50 μM polymyxin-B peptide.

FIG. 4 is a photomicrograph that demonstrates the characteristic fluorescent microscopy image that is observed following the incubation of the nanopatch-containing cells in medium containing 50 µM of the membrane-active polymyxin-B peptide for periods of 5-15 minutes at 25° C.

D. Incubation With a Lipophilic Drug

Figure 5:
FIG. 5 is a fluorescent photomicrograph depicting fluorescence in U937 cells containing lipid/PDA constructs of the present invention following addition of 5 μM lidocaine to the medium containing said cells.

FIG. 5 shows the characteristic fluorescent emission that is observed following the incubation of the nanopatch-containing cells in medium containing 5 µM of lidocaine at 25° C. for periods of between 5 and 15 minutes.

In a further experiment, further aliquots of nanopatch-containing cells were incubated with 1 mM lidocaine under the conditions described hereinabove. Panel A of FIG. 8 presents two views of unperturbed PDA-containing cells, the left half of the panel being a photomicrograph obtained with a fluorescent microscope using an LP 560 nm filter, while the view on the right side was obtained with a transmission differential interference contrast (DIC) microscope. As expected, no fluorescent signal is observable in the image obtained with the fluorescent microscope. After incubation with the lidocaine, however, the characteristic fluorescent emission associated with perturbation of the PDA construct is readily observed (panel B, left side image).

E. Incubation With Melittin

Nanopatch-containing cells, prepared as described above, were incubated with melittin at a final concentration of 5 µM (FIG. 8, panel C), and at 50 µM (FIG. 8, panel D). It may be seen from these photomicrographs (as compared with the unstimulated control in FIG. 8, panel A), that incubation with melittin results in the characteristic fluorescent emission associated with perturbation of the PDA construct. From the difference in signal strength between panels C and D, it would appear that the fluorescent emission is dose-dependent.

F. Incubation With DMPC/Cholesterol Vesicles

Nanopatch-containing cells were incubated with DMPC/cholesterol vesicles, at a final lipid concentration of 0.1 mM, for five minutes (FIG. 8 panel E) and thirty minutes (FIG. 8, panel F) after mixing of the DMPC/cholesterol vesicles with the cells. As may be observed from these micrographs, the interaction of the PDA-containing cells with the DMPC/cholesterol vesicles resulted in fluorescent emission, the intensity of which appears to increase with increasing incubation time.

G. Incubation With Lipoplexes

Figure 6:
FIG. 6 is a fluorescent photomicrograph of U937 cells following addition of lipoplexes to the cell medium.

FIG. 6 demonstrates the fluorescence of the cells that occurs following their co-incubation with lipoplexes for approximately 30 minutes. The lipoplexes used comprise N-[1-(-2,3-Dioleoyloxy)propyl]-N,N,N-trimethylammonium and L-a-Phosphatidylethanolamine, dioleoyl at a molar ratio of 0.72:0.67. The mixture contained a total lipid concentration of 1 mg/ml. 5 µl of this lipoplex solution was added to 60 µl of suspension (approximately 2 million cells).

H. Spectrophotometric Determination of the Color Change Associated With Incubation of Nanopatch-containing U937 Cells With Perturbating Agents In this study, visible-range spectroscopy was used to determine the color changes associated with cell-membrane perturbation caused by (1) oleic acid and (2) poly-L-lysine. Briefly, compounds (oleic acid or poly-L-lysine) were added to samples containing $2\times10^6$ PDA-labeled cells hybrids or approximately 10 µM DMPE/DMPG/PDA vesicles at 1 ml HEPES buffer (the vesicle concentration chosen yielded the same intensity at 640 nm as the cell suspension). Measurements were carried out at 25° C. on a Jasco V-550 uv-vis spectrophotometer, using a 1 cm optical path cell. Spectra were recorded at wavelength range between 450 and 700 nm.

Figures 9A, 9B, 9C:
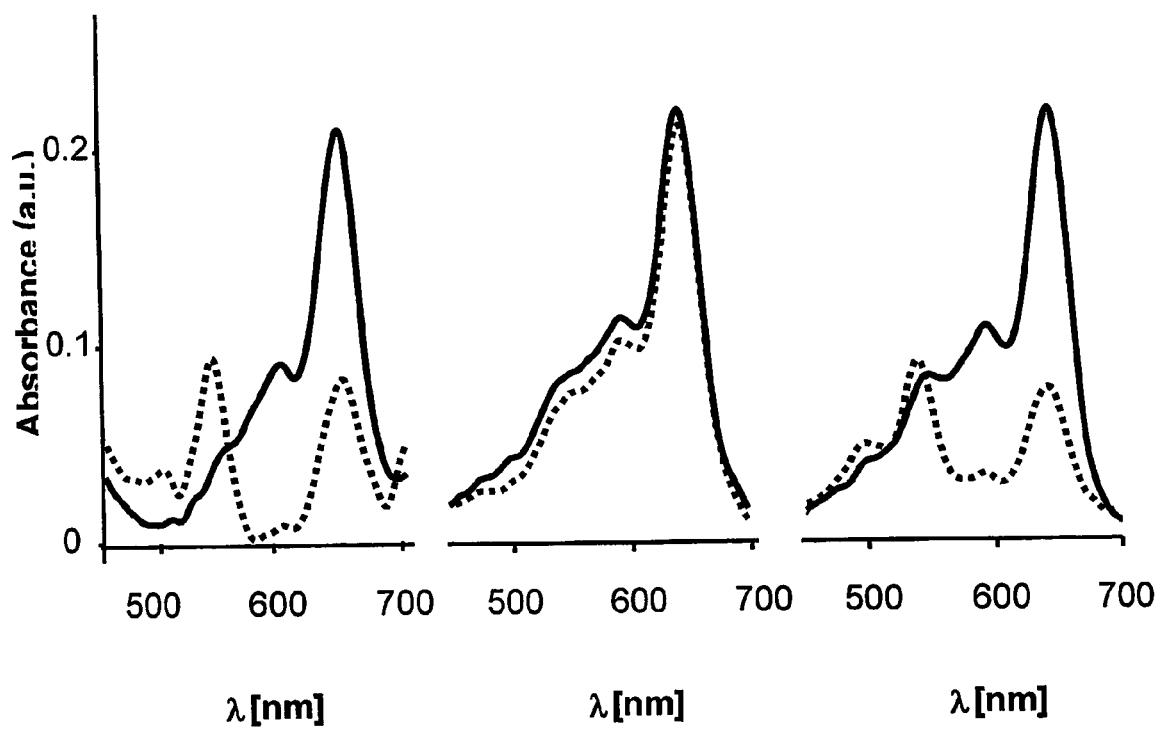
FIG. 9 depicts a series of UV/visible range spectrophotometric spectra obtained from nanopatch-containing U937 cells before (solid lines) and after (broken lines) treatment with oleic acid (A) and poly-L-lysine (B). Graph C presents comparable spectral data for a cell-free lipid polymer vesicle suspension before and after treatment with poly-L-lysine.

The spectrophotometric results obtained are shown in FIG. 9. Graph A presents the data for a PDA-labeled cell suspension before (solid line), and after (broken line) addition of oleic acid at a final concentration of 180 µM. Graph B presents the results for a PDA-labeled cell suspension before (solid line), and after (broken line) addition of poly-L-lysine at a final concentration of 1 µg/ml. Graph C depicts the data for a cell-free DMPG/DMPE/PDA vesicle suspension before (solid line), and after (broken line) addition of poly-L-lysine at a final concentration of 1 µg/ml.

EXAMPLE 5

Detection of Membrane Perturbations Using Nanopatch-containing Neuron Cells 5.1 Cell Culture Preparation Cell cultures were prepared from the Hippocampi of one-day-old rat pups as follows. Tissue was treated for 30 min at 37° C. with 0.25% trypsin (type XI; Sigma), and then gently triturated and the dissociated cells were plated at a concentration of $2\times10^5$/ml onto poly-D-lysine (20 mg/ml; Sigma) and laminin (10 mg/ml; Collaborative Research)—coated glass coverslips. Cells were plated in Eagle's minimal essential medium (MEM) containing 10% heat-inactivated fetal bovine serum (HyClone), 2 mM glutamine, and 0.76% glucose. On the following day, the medium was replaced with fresh SF1C medium [Rayport, D. et al. (1992) *J. Neurosci.* 12, 4264-4280], including B-27 supplements (GIBCO). The cells were grown for up to 12 days in a humid incubator containing 5% $CO_2$/95% air at 37° C. prior to use.

5.2 Fusion of the lipid/monomer assemblies with neurons.

Cells were incubated with DMPE/DMPG/PDA-1:1:6 (mole ratio) vesicles in TG1 buffer (119 mM NaCl, 5 mM KCl, 30 mM Glucose, 32 mM Sucrose, 20 mM Hepes, pH=7.3) for 1 hour at room temperature. Following the fusion, vesicles were polymerized by UV irradiation at 254 nm for 10 seconds and the unbound vesicles were washed 3 times with TG1 buffer.

5.3 Fluorescent Micrography

Figure 7:
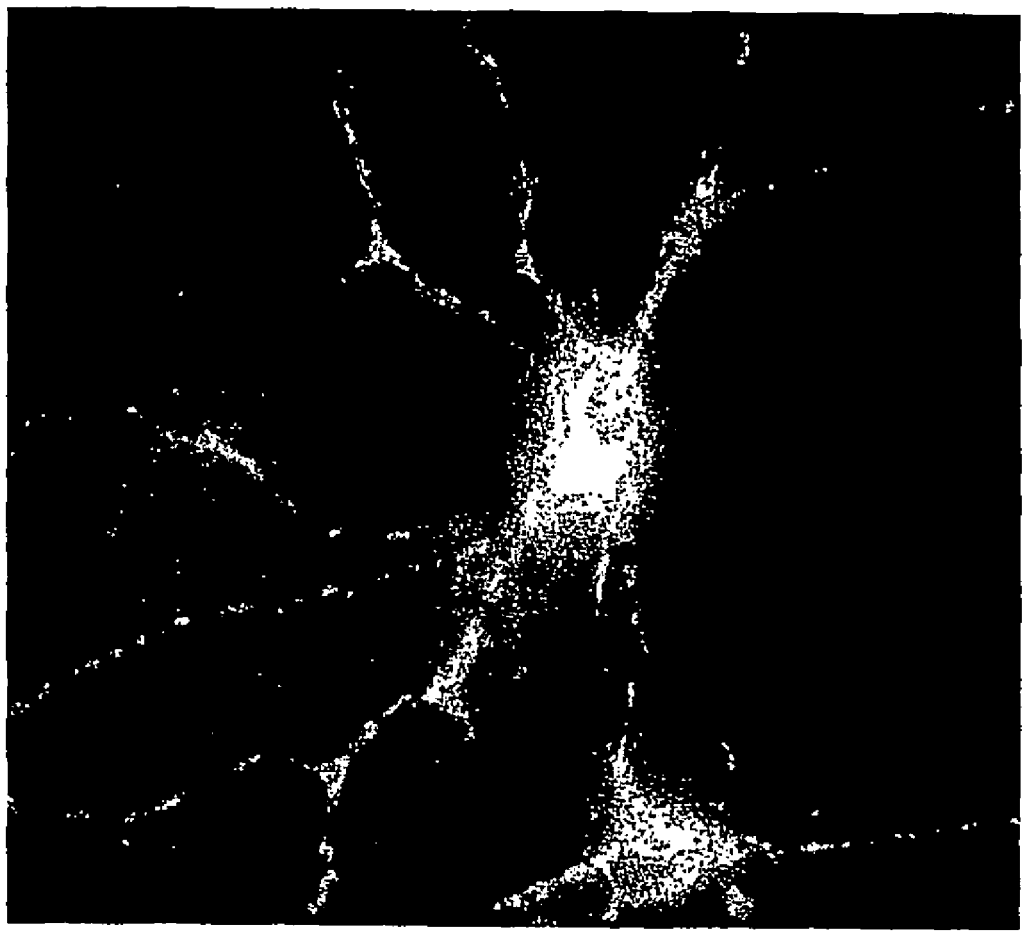
FIG. 7 is a fluorescent photomicrograph of cultured neuronal cells that were isolated from murine brain tissue. The fluorescent light (shown in white) emitted by the cells emanates from the red phase of the polydiacetylene polymer, following incubation of the lipid/PDA/neuron construct in a medium containing 50 mM calcium ions.
Figure 8A:
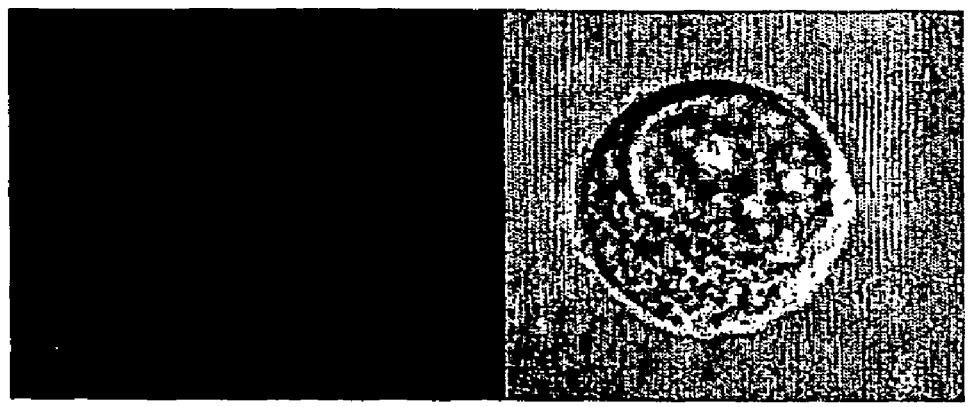
FIG. 8 is series of photomicrographs of nanopatch-containing U937 cells without treatment (A) and after incubation with lidocaine (B), melittin (C,D) and DMPC/cholesterol vesicles (E,F). The left half of each panel is a fluorescent micrograph, while the right half contains a view of the same field obtained using differential interference contrast (DIC) microscopy.
Figure 8B:
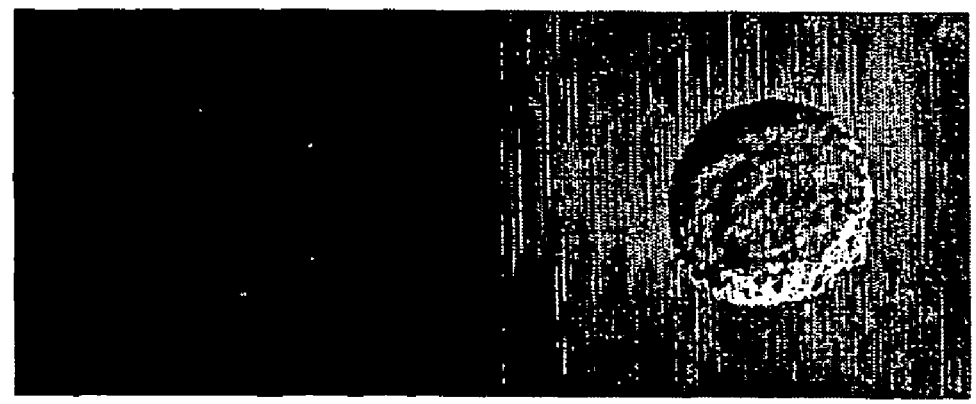
Figure 8C:
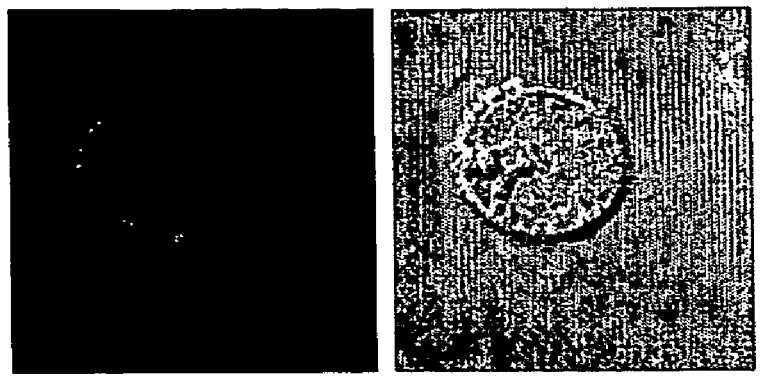
Figure 8D:
Figure 8E:
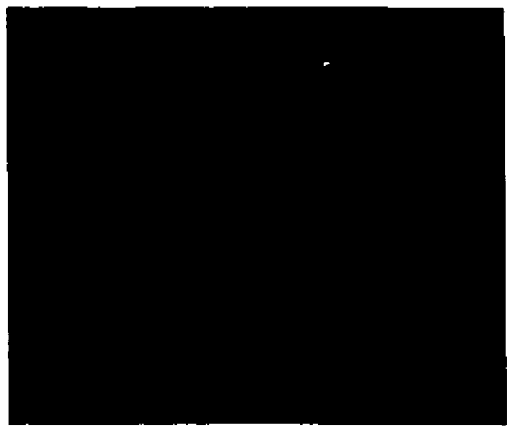
Figure 8E:
Figure 8F:
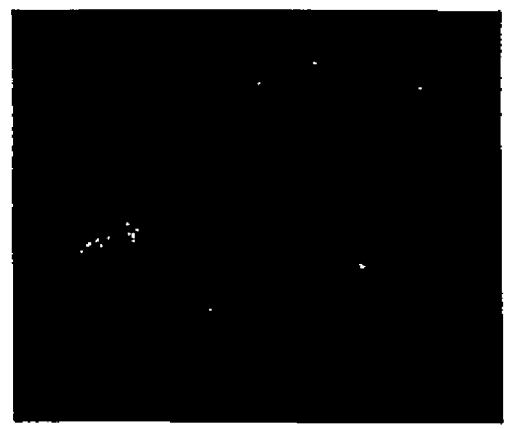
Figure 8F:
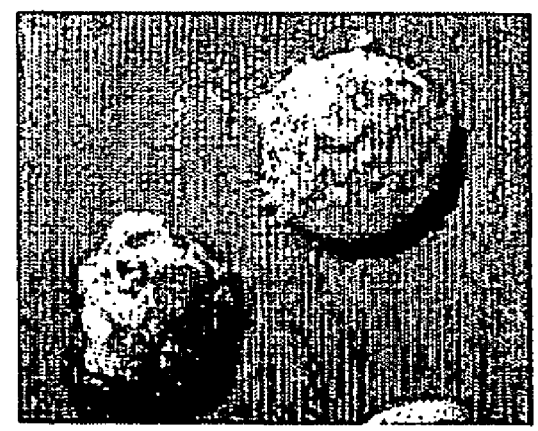

Fluorescent images of the cells were acquired using a Zeiss 200M microscope (Germany) fitted with a CY3 570-650 nm emission range filter (Chroma Technology Corp., Rockingham, Vt.) and CCD cooled camera (PCO). A control image acquired after the polymerization step showed negligible level of the emission intensity. FIG. 7 is a photomicrograph of nanopatch-containing cultured neuronal cells that were prepared as described hereinabove. The white fluorescent light emitted by the cells emanates from the red phase of the polydiacetylene polymer, following incubation of the lipid/PDA/neuron construct in a medium containing 50 mM calcium ions.

EXAMPLE 6

Detection of Membrane Perturbations Using Nanopatch-containing CHO Cells

Figure 10:
FIG. 10 presents phase contrast (left side) and fluorescent (right side) photomicrographs of nanopatch-containing CHO cells following treatment with propranolol. White patches indicate fluorescent emission.
Figure 10:
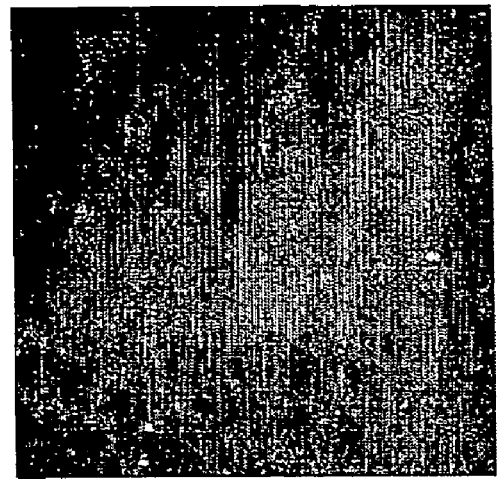

PDA nanopatch-containing CHO cells were prepared as described in Example 1, hereinabove, and treated with propranolol, a membrane-active pharmaceutical compound. FIG. 10 shows phase contrast (left side) and fluorescent (right side) microscope images of the cells following the propranolol treatment, in which the characteristic fluorescent emission associated with perturbation of the PDA-lipid constructs embedded in the cell membrane is readily observed.

EXAMPLE 7

Detection of Membrane Perturbations Using Nanopatch-containing Erythrocyte "Ghosts"

Figure 11:
FIG. 11 presents phase contrast (left side) and fluorescent (right side) photomicrographs of nanopatch-containing erythrocyte "ghosts" following incubation with melittin.
Figure 11:
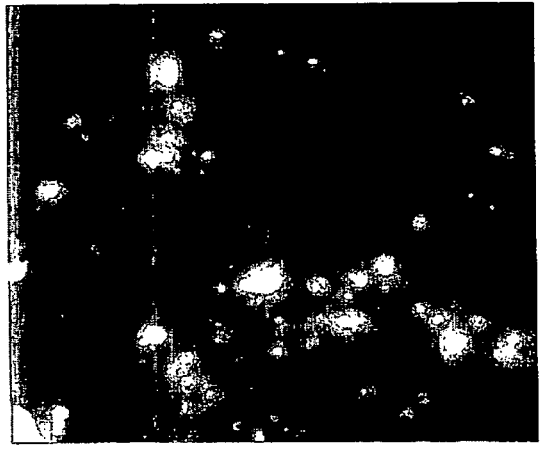

Erythrocyte "ghosts" (i.e. emptied cells) were labeled with DMPC/PDA liposomes, following which the nanopatch-containing cells were treated with the membrane active compound melittin. FIG. 11 shows phase contrast (left side) and fluorescence (right side) microscope images. The fluorescence spots on the right arise from the transformed "red" PDA, induced by membrane interactions of melittin.

EXAMPLE 8

Figure 12:
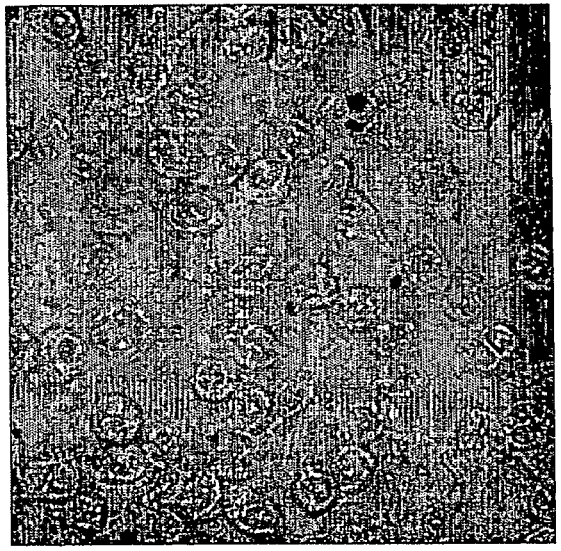
FIG. 12 presents phase contrast (left side) and fluorescent (right side) photomicrographs of nanopatch-containing MCF-7 adenocarcinoma cells, to which the cytotoxic peptide polymyxin B was added.
Figure 12:
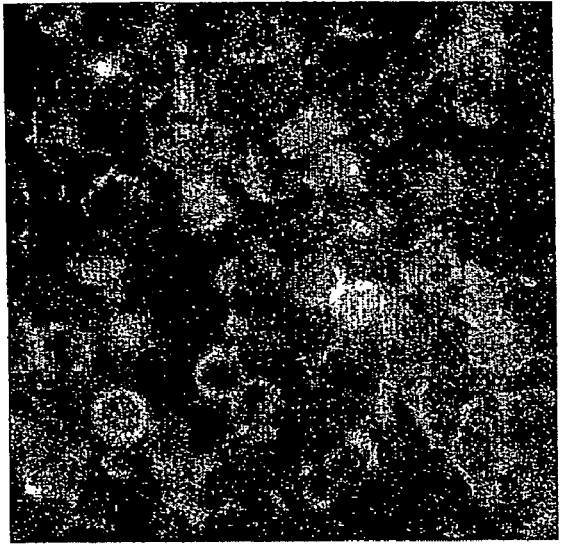
Figure 13A:
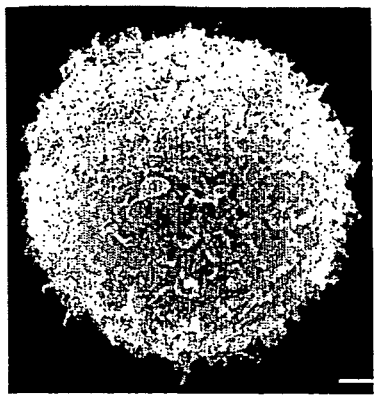
FIG. 13 depicts a series of scanning electron microscope (SEM) (A-C) and transmission electron microscope (TEM) (D) images of U937 cells containing PDA/lipid nanopatches.
Figure 13B:
Figure 13C:
Figure 13D:

Detection of Membrane Perturbations Using Nanopatch-containing MCF-7 Epithelial Cells Nanopatch-containing MCF-7 adenocarcinoma line cells were prepared as described in Example 1, hereinabove. FIG. 12 shows phase-contrast (left side) and fluorescence (right side) microscope images of the neoplastic cells, following addition of the cytotoxic peptide Polymyxin B.

EXAMPLE 9

Electron Microscopic Detection of Nanopatches in U937 Cells

Scanning Electron Microscopy (SEM)

Preparation of samples for SEM experiments was carried out as follows: a suspension of PDA/lipid nanopatch-containing U937 mononuclear cells was prepared as described in Example 1, hereinabove, and added to a tissue culture dish, following which the cells became attached to the plastic surface. Fixation was carried out using a warm fixative (2.5% glutaraldehyde, 2% paraformaldehyde in 0.2 M phosphate buffer) for 30 minutes. Following fixation, samples were washed twice with PBS, dehydrated in a graded series of ethanol solutions, and immersed in graded series of hexamethyldisilazane (HMDS). Following HMDS evaporation, cells were gold-coated and viewed using a QUANTA 200 (FEI Inc.) SEM microscope operating in secondary electron mode.

Transmission Electron Microscopy (TEM)

TEM analysis was carried out using a JEM-1230 model microscope (JEOL, Japan) operating at 80 kV. Cell pellets were fixed with the fixative solution (same as used in the SEM experiments, described hereinabove) at 4° C. overnight. The nanopatch-containing cells were then washed three times with PBS and post-fixated in 1% $OsO_4$, dehydrated stepwise in a graded ethanol series, and were stained during dehydration with saturated uranyl acetate. Cells were embedded in an epoxy resin, sectioned and stained with lead citrate before examination.

FIG. 13 (panels A-C) presents (SEM) images of the prepared cells. Panel A shows the cells following pre-incubation with DMPE/DMPG/PDA vesicles (bar size: 5 μm). The SEM image in panel B depicts part of the membrane surface of the PDA-labeled cells showing bright nano-patches. The broken oval highlights a region with a large number of the patches. (bar size: 1 μm). The image in panel C shows part of the membrane surface of an untreated U937 cell. (bar size: 1 μm). Panel D presents a TEM image of a treated cell, showing dark-staining nano-patches.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. Isolated living cells comprising nanopatch sensors integrated into the cell membrane thereof, wherein said sensors are provided in the form of perturbation-sensitive constructs, and wherein said perturbation-sensitive constructs respond to perturbations of the cell membrane by means of a detectable change in one or more physical or chemical properties associated with said construct, and wherein the nanopatch sensors are prepared prior to fusion into the membranes of living cells.

2. The living isolated cells according to claim 1, wherein the perturbation-sensitive construct comprises a polymer associated with one or more lipid components.

3. The living isolated cells according to claim 2, wherein the polymer is polydiacetylene (PDA).

4. The isolated cells according to claim 3, wherein the PDA is a polymer of 10, 12-tricosadiynoic acid, and the lipid components are selected from the group consisting of dimyristoylphosphatidylglycerol, dimyristoylphosphatidylcholine and dimyristoylphosphatidylethanolamine.

5. The isolated living cells according to claim 1, wherein the detectable change in the physical or chemical properties associated with the perturbation-sensitive constructs is a change in the visible range absorption spectrum of said cells.

6. The isolated living cells according to claim 1, wherein the detectable change in the physical or chemical properties associated with the perturbation-sensitive constructs is a change in the fluorescent emission spectrum of said cells.

7. A process for producing living cells comprising the aforementioned nanopatch sensors according to claim 1, wherein said process comprises the steps of preparing an aqueous solution comprising the perturbation-sensitive construct and co-incubating a suspension of said living cells with said construct such that said construct becomes integrated into the cell membrane of said living cells.

8. The process according to claim 7, wherein the perturbation-sensitive construct comprises a polymerizable material associated with one or more lipid components, and said process further comprises polymerization-inducing short ultraviolet irradiation of the said construct following co-incubation with the living cells.

9. The process according to claim 8, wherein the polymerizable material is a monomer that may be polymerized to form polydiacetylene (PDA).

10. The process according to claim 9, wherein the monomer is 10, 12-tricosadiynoic acid, and the lipid components are selected from the group consisting of dimyristoylphosphatidylglycerol, dimyristoylphosphatidylcholine and dimyristoylphosphatidylethanolamine.

11. A method for detecting and/or measuring agents and conditions that cause perturbations in the cell membranes of living cells, wherein said method comprises the steps of providing isolated nanopatch sensor-containing cells according to claim 1, exposing said nanopatch sensor-containing cells to a known or putative perturbation-inducing agent or condition, and detecting and/or measuring one or more changes in the physical or chemical properties associated with said nanopatch sensors.

12. The method according to claim 11, wherein the perturbation-sensitive construct contained within the nanopatch sensors comprises a polymer associated with one or more lipid components.

13. The method according to claim 12, wherein the polymer is polydiacetylene (PDA).

14. The method according to claim 13, wherein the PDA is a polymer of 10, 12-tricosadiynoic acid, and the lipid components are selected from the group consisting of dimyristoylphosphatidylglycerol, dimyristoylphosphatidylcholine and dimyristoylphosphatidylethanolamine.

15. The method according to claim 14, wherein the change in the physical or chemical properties associated with said nanopatch sensors to be detected and/or measured is a change in the visible range absorption spectrum of said sensors.

16. The method according to claim 15, wherein the change in the physical or chemical properties associated with said nanopatch sensors to be detected and/or measured is a change in the fluorescent emission spectrum of said sensors.

17. The method according to claim 11, wherein the perturbations comprise changes in the three-dimensional conformation of the cell membrane.

18. The method according to claim 11, wherein the perturbations comprise changes in the function of the cell membrane.

19. The method according to claim 11, wherein the perturbations are caused by biochemical processes occurring at the cell membrane surface, and wherein said processes do not cause any significant structural or functional changes within said cell membrane.

20. Isolated living prokaryotic cells comprising nanopatch sensors integrated into the cell wall and/or cell membrane thereof, wherein said sensors are provided in the form of perturbation-sensitive constructs, and wherein said perturbation-sensitive constructs respond to perturbations of the cell wall and/or of the underlying cell membrane by means of a detectable change in one or more physical or chemical properties associated with said construct, and wherein the nanopatch sensors are prepared prior to fusion into the membranes of said living cells.

21. The isolated prokaryotic cells according to claim 20, wherein the perturbation-sensitive constructs comprise a polydiacetylene (PDA) polymer associated with one or more lipid components selected from the group consisting of dimyristoylphosphatidylglycerol, dimyristoylphosphatidylcholine and dimyristoylphosphatidylethanolamine.

22. The isolated prokaryotic cells according to claim 20, wherein the detectable change in the physical or chemical properties associated with the perturbation-sensitive constructs is a change in the visible range absorption spectrum of said cells.

23. The isolated prokaryotic cells according to claim 20, wherein the detectable change in the physical or chemical properties associated with the perturbation-sensitive constructs is a change in the fluorescent emission spectrum of said cells.

24. A process for producing living prokaryotic cells comprising the aforementioned nanopatch sensors according to claim 20, wherein said prokaryotic cells have a cell wall as their outer layer, and wherein said process comprises the steps of preparing an aqueous solution comprising the perturbation-sensitive construct and co-incubating a suspension of said living cells with said construct such that said construct becomes integrated into the cell wall and/or cell membrane of said cells.

25. The process according to claim 24, wherein the perturbation-sensitive construct comprises a polymerizable material associated with one or more lipid components, and said process further comprises polymerization-inducing short ultraviolet irradiation of the said construct following co-incubation with the living cells.

26. The process according to claim 25, wherein the polymerizable material is 10, 12-tricosadiynoic acid, and the lipid components are selected from the group consisting of dimyristoylphosphatidylglycerol, dimyristoylphosphatidylcholine and dimyristoylphosphatidylethanolamine.

27. A method for detecting and/or measuring agents and conditions that cause perturbations in the cell walls and cell membranes of living cell-wall containing prokaryotic cells, wherein said method comprises the steps of providing isolated nanopatch sensor-containing cells according to claim 20, exposing said nanopatch sensor-containing cells to a known or putative perturbation-inducing agent or condition, and detecting and/or measuring one or more changes in the physical or chemical properties associated with said nanopatch sensors.

28. The method according to claim 27, wherein the perturbations comprise changes in the three-dimensional conformation of the cell wall and/or cell membrane.

29. The method according to claim 27, wherein the perturbations comprise changes in the function of the cell wall and/or cell membrane.

30. The method according to claims 27, wherein the perturbations are caused by biochemical processes occurring at the cell wall surface and/or cell membrane surface, and wherein said processes do not cause any significant structural or functional changes within said cell wall and/or cell membrane.

* * * * *